United States Patent [19]
Coomer

[11] Patent Number: 5,647,147
[45] Date of Patent: Jul. 15, 1997

[54] PROSTHESIS SHOE INSERT FOR PROPULSIVE CONDITIONING

[76] Inventor: Sven Coomer, 1136 Terminal Way Suite 208B, Reno, Nev. 89502

[21] Appl. No.: 251,616

[22] Filed: May 31, 1994

Related U.S. Application Data

[63] Continuation-in-part of Ser. No. 22,323, Feb. 26, 1993, abandoned.

[51] Int. Cl.⁶ .................................. A43B 7/14; A61F 5/14
[52] U.S. Cl. .................................. 36/93; 36/153
[58] Field of Search .................................. 36/43, 44, 71, 36/93, 28, 153, 154

[56] References Cited

U.S. PATENT DOCUMENTS

| | | | |
|---|---|---|---|
| 2,339,993 | 1/1944 | Hollander | 36/11.5 |
| 4,128,951 | 12/1978 | Tansiu | 36/44 |
| 4,130,948 | 12/1978 | Krug | 36/44 |
| 4,305,212 | 12/1981 | Coomer | 36/29 X |
| 4,633,877 | 1/1987 | Pendergast | 36/44 X |
| 4,962,762 | 10/1990 | Beekil | 36/44 X |
| 5,067,257 | 11/1991 | Coomer | 36/93 |

FOREIGN PATENT DOCUMENTS

| | | | |
|---|---|---|---|
| 578325 | 8/1976 | Switzerland | 36/71 |

*Primary Examiner*—B. Dayoan
*Attorney, Agent, or Firm*—William H. Maxwell

[57] ABSTRACT

An orthotic footbed insert for athletic shoes and boots, wherein contiguous top and bottom laminates form an envelope that is carried by a premolded stabilizer and injected with a two-part liquid resin that fills all space within the envelope when inserted into a shoe or boot with a person's foot in situ therein and positioned on a supporting platform having angularly inclined tarsal and talar planes enforceably dorsiflexing the footbed when the injected liquid cures.

19 Claims, 4 Drawing Sheets

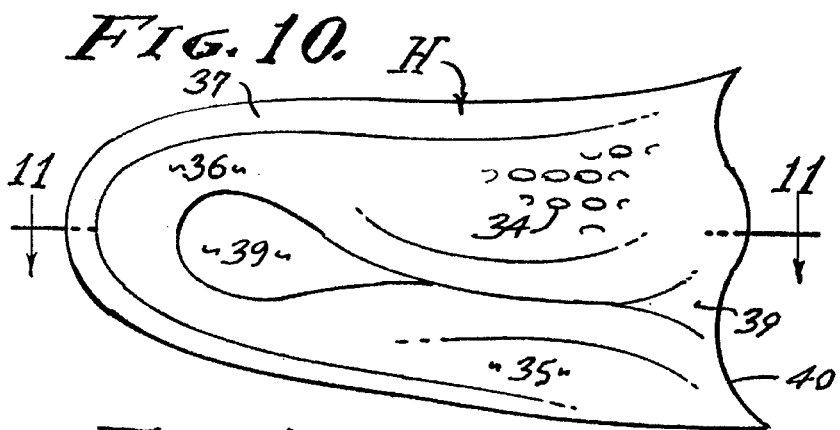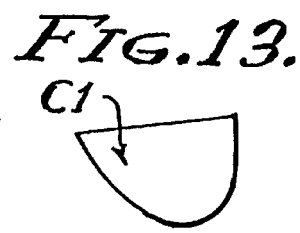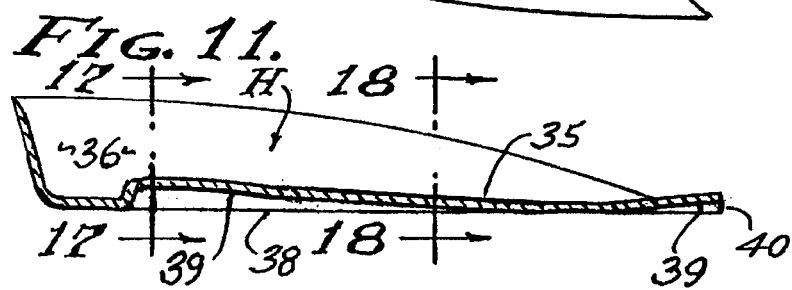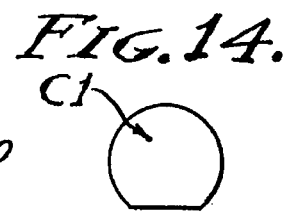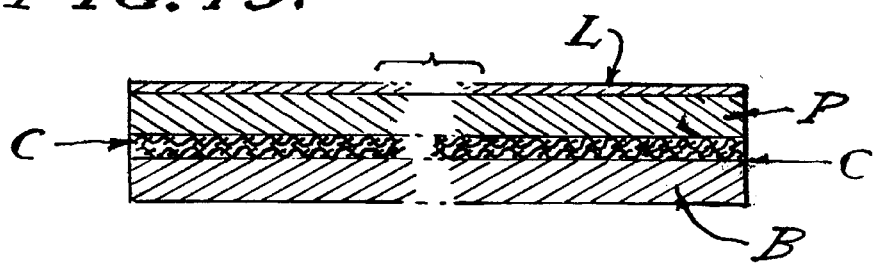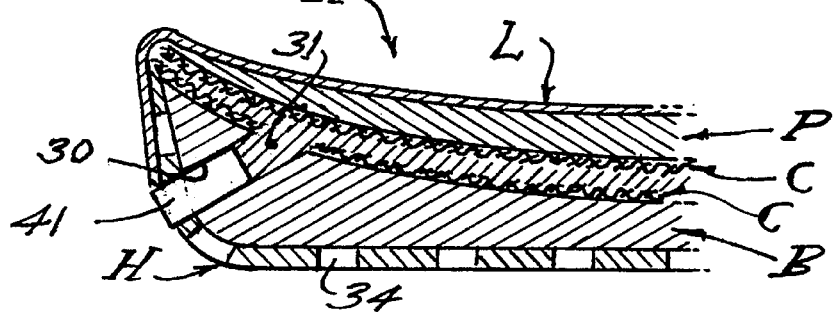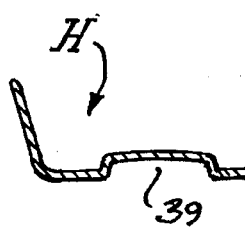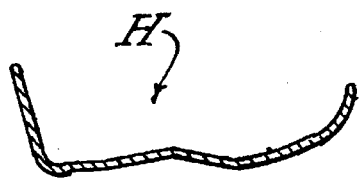

PROSTHESIS SHOE INSERT FOR PROPULSIVE CONDITIONING

This application is a continuation in part of Ser. No. 08/022,323, filed Feb. 26, 1993, now abandoned.

BACKGROUND OF THE INVENTION

This invention relates to footwear and particularly to a prosthesis used "in addition to" (Webster) the plantar portion of a person's foot, it being an object of this invention to provide an orthotically correct plantar insert for foot support during normal and abnormal activities, and including athletic activities. It is also an object of this invention to provide a planar insert that supportably embraces the plantar portion of the foot in an optimum disposition for the lever function of the foot, for example in the propulsion mode.

The present invention is an improvement over and an implementation of features disclosed in my prior U.S. Pat. Nos. 4,305,212 issued Dec. 15, 1981 and 5,067,257 issued Nov. 21, 1991. U.S. Pat. No. 4,305,212 entitled ORTHOTICALLY DYNAMIC FOOTWEAR discloses a shoe incorporating dynamic Orthotic means which adapt to the foot in a prescribed manner, controlling heel "strike" and weight bearing loads, establishing a cup-shape to "catch" the heel and foot to stabilize it, balancing and maintaining the sub-talar joint in a neutral attitude and the mid-tarsal joint locked, enabling the foot and ankle so maintain optimum integrity as an efficient support and propulsion system, and resisting the symptomatic tendency for the sub-talar joint to overcompensate and overstress the anatomy. U.S. Pat. No. 5,067,257 entitled INJECTION FITTED BOOT LINER discloses a protective liner custom fitted by low pressure fluid injection over a wearer's anatomy, by permeation of select areas of porous padding, surrounding areas of non-porous padding, with an impervious membrane occluding portions of the porous padding to control fluid resin penetration and with scarfed abutment of padding for gradual softness variation, including a method by which a pair of liners are simultaneously injected with fluid resin while the wearer's anatomy is in place, for hardening of the fluid and of the permeated padding. The improvement herein lies in the implementation of a plantar insert that is incorporated or inserted into the shoe, the plantar insert being characterized by a laminate article of materials that simulate the plantar body tissue of the human foot. And further, pre-selected cushion inserts are strategically placed, especially for comfort and for protection against bony prominences, namely heel impact and metatarsal impact.

It is an object of this invention to implement the aforementioned improvements in an article of manufacture, and a method of making the same, all of which is simple and practical and with ensured results.

Numerous manipulative methods have been proposed for finding and positioning the joint processes of the foot in order to achieve a neutral sub-talar joint and locked mid-talar joint, for the purpose of molding and fabricating prosthetic footwear. Reference is made to propulsive postures created within lasted forms of track and other field event shoes, bicycle racing shoes and ice skating and ski boots, as they have been used in the recent past without underfoot prosthesis considerations. Orthotically, there is a neutral and locked alignment of the foot to be considered as the optimum centered and balanced position for bearing weight with minimal stress and fatigue. For example, research has demonstrated that there is minimum firing of muscles in maintaining balance when an optimum balanced positioning of the foot is maintained, and which is interpreted as reducing stress and fatigue.

The accepted methods of optimum foot positioning are either the unweighted (seated, prone, or supine) or the weighted (standing) positions. When unweighted the technician, that is the person in charge of implementing this insert, dorsiflexes the ankle joint against resistance by applying upward pressure to the head of the fifth metatarsal with one hand, and feels for a neutral alignment of the mid-tarsal joint under the thumb and forefinger with the other hand. When neutral is felt, the foot position is held until the molding materials catalyze, cool and cure to the shape of the foot's planar surface. When weighted, the techician positions the mid-tarsal joint, feeling again with the thumb and forefinger by rotating the shaft of the tibia inward or outward. However, displacement of soft tissue and one joint alignment becomes difficult when the foot is weighted, since with each procedure there are different displacements of tissue and bone which affect the supporting interface configurations. Accordingly, it is an object of this invention to provide a plantar insert whereby either unweighted or weighted molding methods are acceptable and highly successful, as circumstances may require.

There are various methods for applying molded materials to the foot, the most sophisticated of which uses atmospheric pressure to suck the resin materials against the foot, by sealing them off within a plastic bag and then evacuating the air with a pump.

The most commonly used molding method is the weight bearing method. The resin materials are usually counter pressed against the foot by a variety of foam shapes and densities. Another method is to insert a heated plastic sheet or foam into the shoe and allow the person being fitted to dynamically mold the plastic while it cures, as by walking about. In accordance with this invention, a plantar insert procedure is used so that the foot is positioned according to a unique biomechanical technique, whereby a technician has complete control and flexibility to use full-weight bearing, semi-weight bearing or non-weight bearing methods in attaining the required orthotic positioning and optimum supportive positioning of the prothesis.

It is an object of this invention to simultaneously mold a pair of prostheses, as thus far described, enforcing neutral and locked alignment by the pre-molded plantar inserts. This minimizes the total weight and volume of resin needed to fill the inherent spaces that occur between the plantar insert and the shoe interior, and the differences between the premolded plantar insert shape and the shape of the individual's foot in its neutral and locked alignment. Therefore, with this invention a vacuum is not necessary to suck the molding resin materials up and hold them against the foot. On the contrary, soft foot tissue is conformed to by the soft tissue simulating resin material and so that the customized molding is carried out effectively with or without weight bearing.

In accordance with this invention, it is an object that this biodynamic phenomenon is used to position and then mold the quite specific plantar shapes into the optimum position for the prosthetic foot support, while selecting the appropriate resin materials which allow for the normal adaptive motions and foot functions. It is therefore an object of this invention to provide a plantar insert for the centered and neutral position from which all movements originate and to which they return. The resulting prosthesis encourages good posture rather than poor off-balance posture that produces stress and could cause injury.

SUMMARY OF THE INVENTION

This invention provides a shoe prosthesis in the form of a pre-molded plantar insert that enforeces propulsive conditioning of the foot, and which has an orthotic function that provides coextensive neutral and locked support for custom molding of shoes and boots in the propulsion mode. In practice, this plantar insert is comprised of an envelope having a central injection passage for the reception of a charge of silicon resin that solidifies and cures into a relatively soft body that simulates the soft tissue of the plantar portion of the human foot. The top surface and perimeter of the porous body is sealed with an impervious liner contiguous therewith, and all of which is substantially flexible as is the sole of the shoe or boot into which it is inserted. A padding of non-permeable foam material coextensively underlies the foot engaging surface of the plantar insert, a feature being the installation of permeable insert members at strategic areas of the non-permeable padding, such as those areas which occur beneath the heads of the metatarsal and sub-talar processes. Also, a feature is the peripheral escapement of air from the envelope when so desired, and the uniform solidification of the tissue simulating silicon plastic.

The foregoing and various other objects and features of this invention will be apparent and fully understood from the following detailed description of the typical preferred forms and applications thereof, throughout which description reference is made to the accompanying drawings.

THE DRAWINGS

FIG. 1 is a side view of an athletic shoe broken away to show the plantar insert in section.

FIGS. 2 and 3 are sectional views taken as indicated by lines 2—2 and 3—3 on FIG. 1.

FIG. 10 is a bottom view of the heel stabilizer member.

FIG. 11 is a sectionnal view of the heel stabilizer member taken as indicated by line 11—11 on FIG. 10.

FIGS. 12 through 14 are plan views of the selectable cushion members that are inserted into the recesses shown in FIG. 7.

Figure 4:
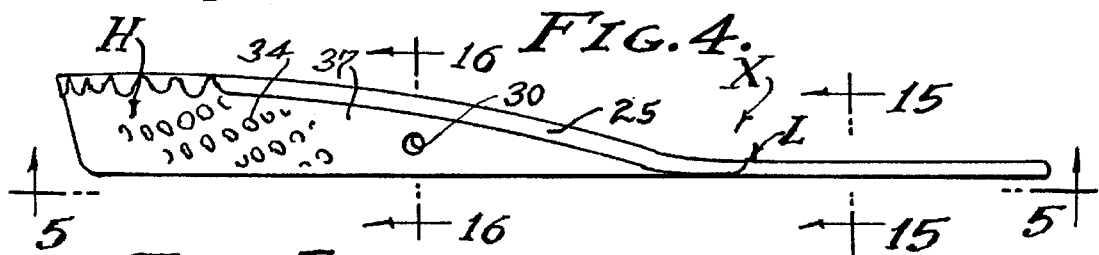
FIG. 4 is a side elevation of the insert removed from the shoe.
Figure 5:
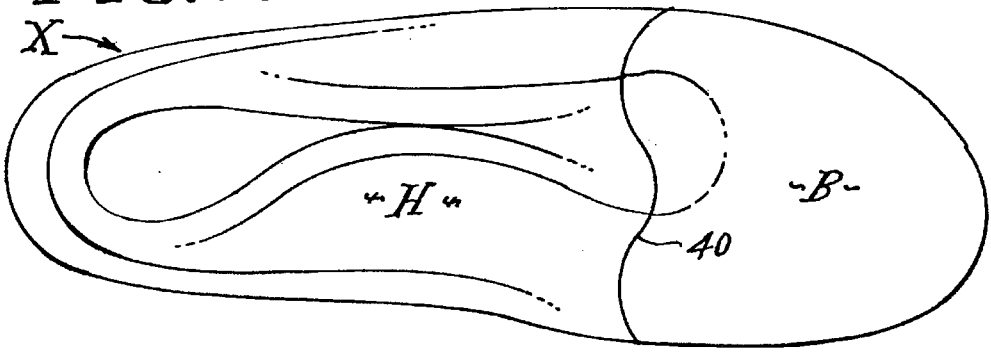
FIG. 5 is a bottom view of the insert taken as indicated by line 5—5 on FIG. 4.

FIGS. 15 and 16 are enlarged fragmentary sectional views of the laminated members, taken as indicated by lines 15—15 and 16—16 on FIG. 4.

FIGS. 17 and 18 are sectional views of the heel stabilizer, taken as indicated by lines 17—17 and 18—18 on FIG. 11.

Figure 19:
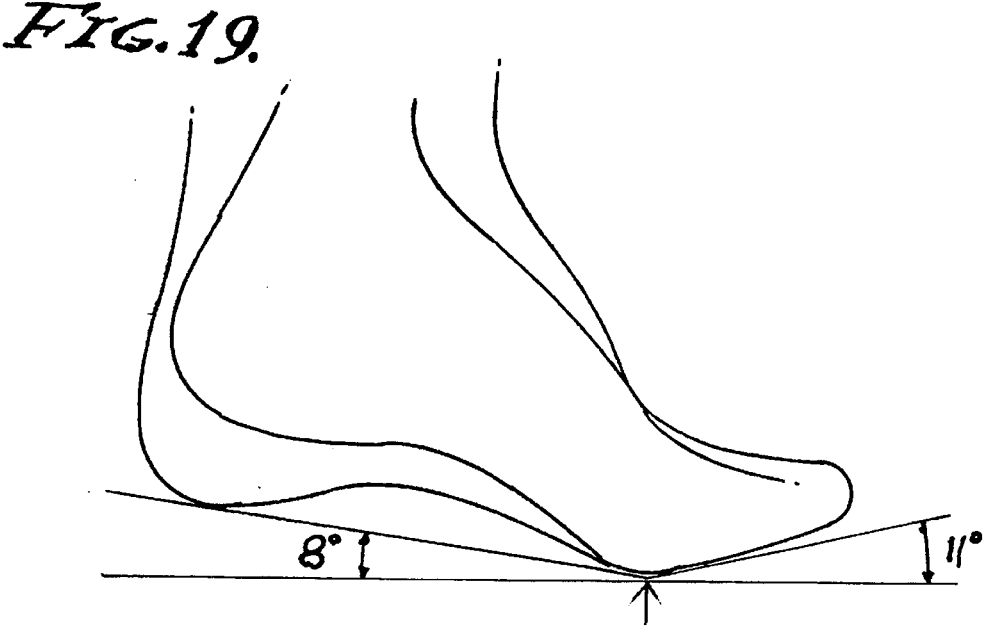

FIG. 19 is a two position diagram of the human foot, illustrating the dorsiflexed condition enforced by this invention, and the toe-off position achieved thereby.

Figure 20:
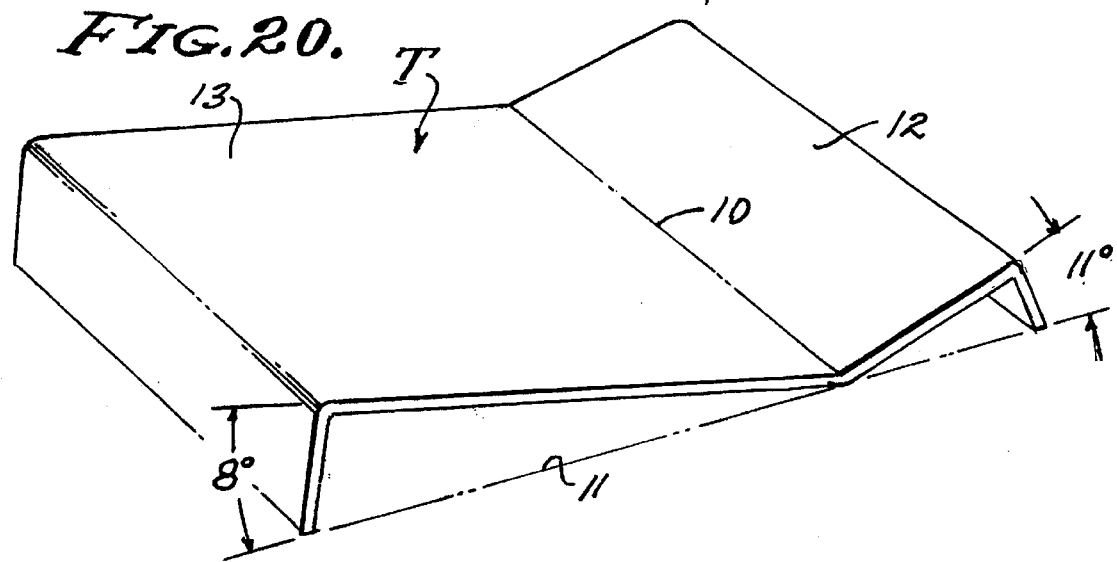

And, FIG. 20 is a perspective view of the dorsiflex enforcement platform and its angular talar and tarsal support planes.

PREFERRED EMBODIMENT

Figure 1:
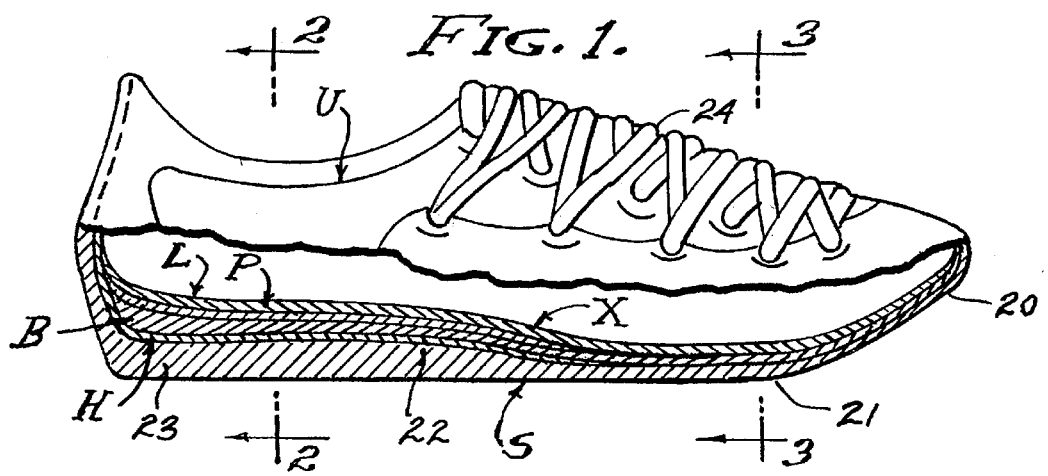

This invention relates to custom fitted orthotic footwear, such as an athletic shoe insert molded to an individual's foot. The shoe shown in FIG. 1 is comprised of a sole S that underlies the plantar surface of the foot, and an upper U that extends from the sole to enclose the foot while exposing the ankle. The sole S is an elongated member made of flexible and depressible material that is resilient, and adapted to be distorted by force and to return to its original shape. As shown, the upper U is provided for holding the sole S securely and comfortably to the foot, and is essentially a wrapping that embraces and positions the foot for plantar support upon the sole S.

The construction of the sole S will vary and is typically made of a flexible and resiliently depressible elastomer material, and comprised of a toe portion 20, a ball portion 21, an arch portion 22, and a heel portion 23. These portions are integrally formed and usually molded as one element to underlie the plantar portion of the foot to which they are correspondingly complementary. That is, the corresponding plantar areas of the shoe sole S and the individual's foot are coextensive.

The upper U can vary in style and in choice of materials, and is a supple cover of leather or woven material form fitted to the contoured last configuration of the individual's foot, to cover the ball and arch portions and to wrap around the heel portion in conformity to the foot configuration. However, perfection in this respect is difficult to attain and is highly improbable. Accordingly, this invention provides a system by which a perfect fit, comfort and improved performance is attainable.

As shown, double lacing 24 is employed to extend over the arch of the foot and to the toe portion thereof and overlying the ball portion of the sole S. The upper U is flexible so as to bend with the mid-tarsal process and to turn with the sole S and in practice is tightly held to the foot by the lacings 24. The sole S configuration hereinabove described is made of compressible material such as rubber-like elastomer, the flexibility, resilience and hardness of which is determined as circumstances require for functionally controlling foot configuration changes. That is, the material as related to thickness of the sole formation determines flexibility and compressibility or softness thereof which permits the distortions which establish the various degrees of departure from original form in the simulation of walking or running in sand or the like, thereby applying a very natural alignment of forces along the tibia axis and through the neutral sub-talar processes and locked mid-tarsal processes.

Figure 2:
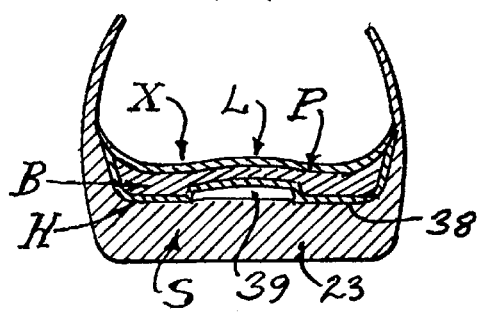
Figure 3:
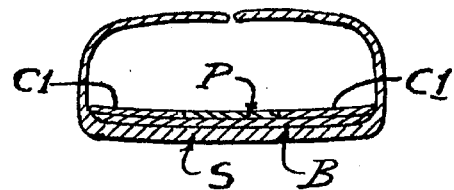

Referring now to the plantar insert X with which this invention is primarily concerned, a laminate characterized by an impervious body member B that is pre-molded of non-porous closed cell foam material and solidified into a last formation to closely fit the foot to which it is to be applied, is placed coextensively over the sole S. As shown in FIG. 1 the plantar insert X is contiguously fitted to the upper facing contour of the sole S, and its periphery is defined by the interior of the upper U where said upper joins the sole (see FIGS. 2 and 3). In practice, the thickness of the plantar insert X varies as it extends from toe to heel, being thicker at the heel. It is to be understood that the plantar insert X is made in a range of sizes and is peripherally contoured to be complementary to the shoe or boot lasts to which it is applied. A typical configuration is shown.

Figure 6:
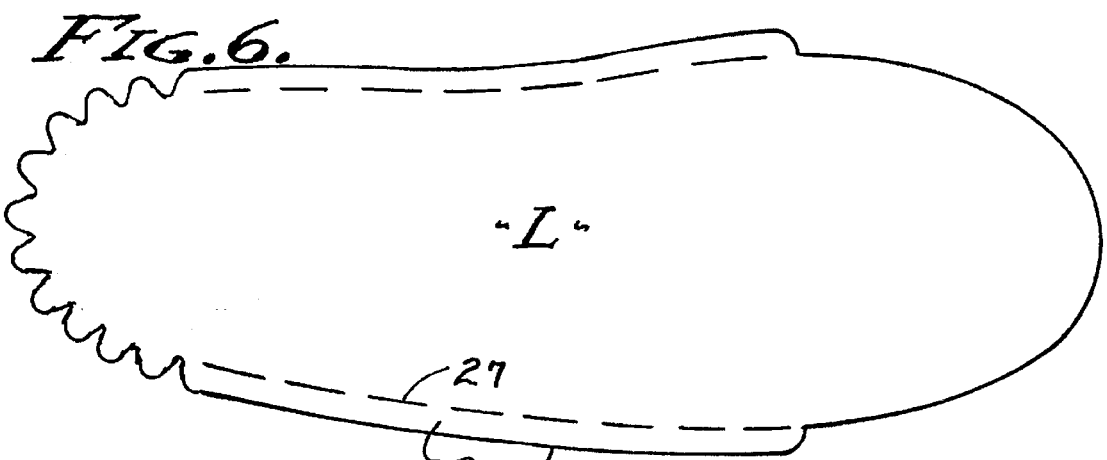
FIGS. 6 through 9 are plan views of the laminate member of the insert, FIG. 6 being the liner member, FIG. 7 being the padding member, FIG. 8 being the cloth coupling member, and FIG. 9 being the non-porous body member.

Referring now to FIG. 6 of the drawings, a liner member L is the top protective skin of the plantar insert X. In practice, the liner member L is a very thin flexible and supple sheet of material having a marginal portion 25 extending around the heel and instep areas and presenting a surrounding margin or edge 26, for example 10 mm outside the periphery of the finished insert X as shown and described herein. The underside of the liner member L is cemented or otherwise secured to a padding member P, as for example by an adhesive coating applied coextensively thereto. The periphery of the sole area is continued in a line of demarcation 27 that is applied to the liner member L for its exact location on and over the padding member P. The margin is interrupted as it extends around the heel, in order to facilitate folding, as shown.

The liner member L is the plantar support surface which is flexible and supple and of a texture having a softness similar to that of the plantar tissue of the foot which it opposes. Accordingly, the liner member L is preferably made of a non-porous material or a semi-porous material that will function as a physical barrier between the insert X and the person's foot. A preferred liner material is an artificial leather such as LORICA® manufactured by Lorica S.P.A. of Milan, Italy, a supple soft leather-like material accepted in the art as an inner sole facing. The under side of liner member L is adhered to the top side of the padding member P next described, a cement or adhesive being applied therebetween.

Figure 7:
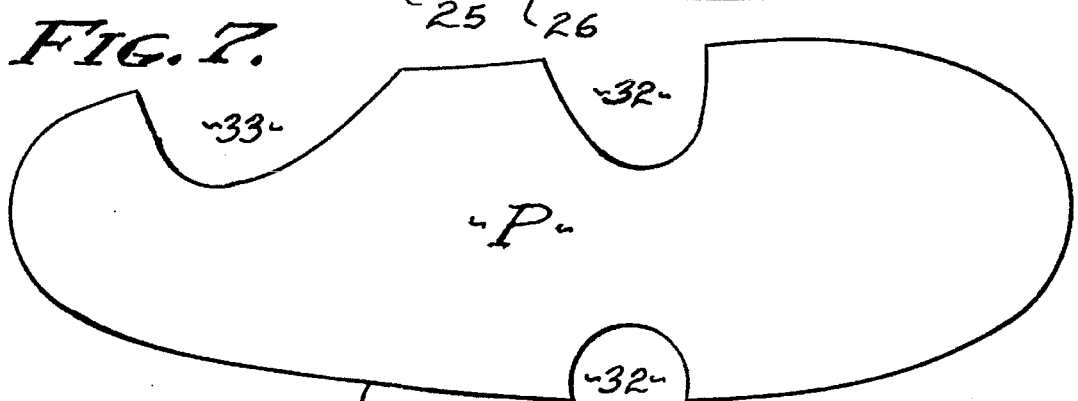

Referring now to FIG. 7 of the drawings, the padding member P is coextensive with the overlying liner member L, as defined by the periphery of the sole portion and the line of demarcation 27. The member P is preferably a uniform thickness of soft non-porous closed cell Ethyl Vinyl Acetate foam plastic, or a like material. In practice, the member P is approximately 2 mm thick with at least one metatarsal opening or void therethrough, and at least one talar opening or void therethrough. The matatarsal openings are shown as recesses 32 in the padding periphery 28, and the talar opening or openings are shown as recesses 33 in the padding periphery 28. As shown, the recesses 32 and 33 are provided to receive permeable cushions C1 and C2 later described. A feature is that the recesses open at the periphery of the padding member P to receive the cushions which are selected to customize the insert X.

The underside of the padding member P is initially free of and coextensively overlies the body member B, preferably with a coextensive backing or coupling cloth C adhered to its underside (see FIG. 8), secured as by an adhesive material coextensively applied therebetween. In practice, the coupling backing or cloth C is a loose weave such as cheese cloth or a knit material that permits interface adhesion between the padding member P and body member B next described. This feature ensures that these members will not delaminate when subjected to shear stresses imposed by plantar forces. Another feature is that the periphery 28 of the padding member P coincides with the line of demarcation 27 and with the periphery of the front sole portion.

Figure 8:
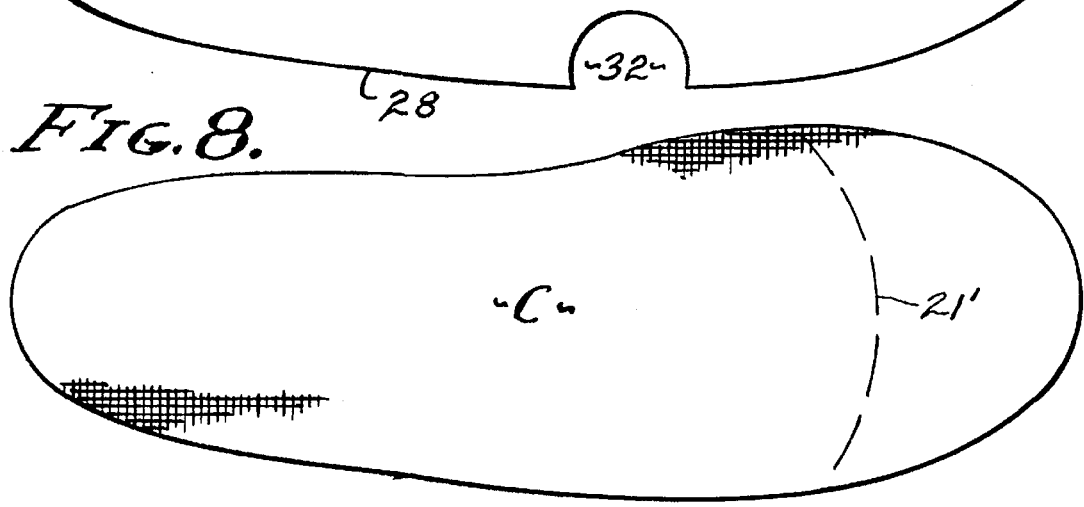
Figure 9:
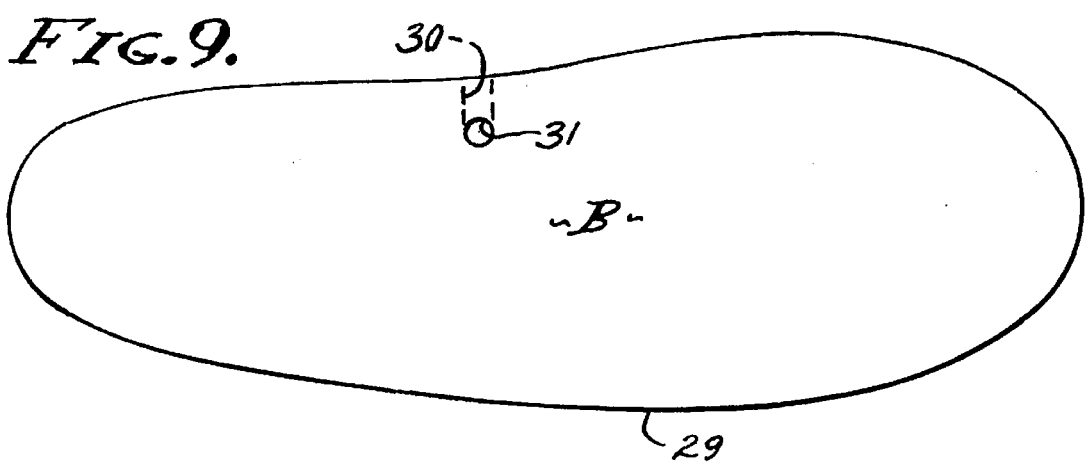

Referring now to FIG. 8 of the drawings, the body member B is a flexible intermediate solid disposed between the shoe sole S and the plantar surface of the person's foot, the liner member L thickness being nominal. In practice, the initial thickness of the body member B, before resin injection, is adequate to adjust to spaces and/or cavities that will inherently develop as a result of discrepancies between the shoe last interior and the individual's foot anatomy. Preferably, the body member B is made of closed cell foam material that will bond to the injected silicon resin when it solidifies. A polyethylene foam is used.

The body member B is wedge-shaped from heel to toe, having a periphery 29 matching the periphery 28 of the padding member P. A feature of the flexible body member B is an injection passage 30 with a central discharge 31 entering laterally therein through its top surface, for receiving a charge of fluid resin as later described. The central discharge 31 of the injection passage 30 ensures displacement of air to and from the periphery 29 without entrapment. Thus, the fluid resin displaces all air and cures in a solid uninterrupted mass within the envelope formed between the top laminations L, P and C, and bottom laminations B and C.

Referring now to FIG. 17 of the drawings, the padding P overlying liner L and underlying the backing or coupler cloth C are also assembled face to face in laminate form with adhesive material therebetween. Separately, the aforesaid body member B and backing or coupler cloth C are assembled face to face in laminate form with adhesive material therebetween, and supported within a heel stabilizer member H shown in the form of an upwardly open shell coextensive with the heel and instep of the sole S.

These two laminates of members L, P and C, and of members B and C are separately brought together with their respective peripheries coinciding to form an envelope, by folding down the uppermost marginal edge 25 of the liner member L and securing it over the outer peripheries of member B and C, and secured with a cement or adhesive. In practice, the toe area defined by a typical line of demarcation 21' is coextensively secured with the same application of cement or adhesive.

The heel stabilizer H is substantially rigid high density non-porous foam plastic, preferably Ethyl Vinyl Acetate sheet that is coextensively perforated with equally spaced slits 34, and of approximately 1 mm thickness, a material that can be stretched, flattened and formed with heat and under pressure into the desired shape as shown herein. The shell-form of the heel stabilizer H is comprised of an arch or instep portion 35 and an upwardly open cup portion 36 that embraces the heel and taler process of the foot, and defined by a surrounding upwardly standing side wall 37 extending around the posterior of the heel. The bottom plantar face 38 is essentially flat and planar, as it underlies the heel and instep portions of the above described laminate members, the supporting plantar surface of the heel stabilizer H having a depending peripheral rib of increased depth as compared with the center area of the shell H and extending from the instep portion along the outside of the heel portion and continuing around the back of the heel portion to the inside thereof and thereby establishing an underlying cavity 39 extending longitudinally of the underside of the heel stabilizer H. It will be observed that the slit shaped perforations are stretched into oval and substantially round perforations and remain closed slits in areas that are not stretched. The front edge 40 of portion 35 and top edges of the walls 37 are gradually flattened to sharp or feature edges, as shown. The underlying cavity 39 is of increased depth above the lower support plane of the stabilizer shell, in the areas underlying both the metatarsal and sub-talar processes of the foot, thereby providing bubble-like formations subject to depression when weight is applied. The bubble-like formations of the cavity 39 are effective when impacts are experienced.

The outwardly extending marginal portion 25 of the liner member L is turned down to lie contiguous to the periphery 28 of the padding member P and against the wall 37 of the heel stabilizer H, and adhered thereto by the adhesive material applied coextensively thereto. The injection passage 30 is open at one side of the body member B and opens centrally within said envelope of laminates, from where the fluid resin flows divergently as indicated by the divergent arrows. The completed plantar insert is used by injecting it with a two part impression type silicon resin having, for example, a five minute pot life and that solidifies to a softness simulating the fleshy body tissue of the plantar portion of the human foot. Such a plastic material remains flexible and substantially incompressible in its solid state. However, being plastic, it does flow and thereby permits limited variation in foot displacement as working pressures are applied.

Referring now to FIG. 7 of the drawings, cushion members C1 and C2 are provided for placement under critical processes. As shown, the mid-tarsal recesses 32 are occupied by cushions C1 of selected density, and the talar recess 33 is occupied by a cushion C2 of selected density. Unlike the body member B, the cushions C1 and C2 are inserts of sponge-like material that will accept a charge of fluid resin that then solidifies therein. Accordingly, the cushions C1 and C2 are made of breathable foam such as virgin T.H.W. or recycled polyurethane known as AGGLOMARATO®. A feature is that when the silicon resin cures, the foam cushion inserts C1 and C2 solidify in situ, in the desired interface shape of the foot. The cushions C1 and C2 are prefabricated different densities of foam and of varied thickness, and they are selected for their required biomechanical support.

Referring now to FIG. 20 of the drawings, the molding platform T is shown with its preferred angles of metatarsal dorsiflexion from the supporting plane 11. There is a transverse gutter 10 that underlies the metatarsal processes and from which the front plane 12 rises at approximately 11°, and from which the rear plane 13 rises approximately 8°.

TECHICIAN PROCEDURE

Approximately 15 grams (depending on size) of a two part silicon resin (Wacker ADS 921) is injected into each insert X, using a manual pump and static mixing tube, the resin being applied through passage 30. After permeating the porous body member B and cushions C1 and C2 the passage 30 is closed with a plug 41. The protheses, the two inserts X, are massaged fore and aft in order to distribute the fluid mass uniformly, and any excess resin and air removed through the periphery 29. The two prosthesis inserts X are then inserted into position within the pair of shoes to be customized.

The person's feet are inserted into the shoes and the shoes laced or otherwise closed in a normal manner, and the person stands upon the molding platforms T with the metatarsal heads aligned with the gutters 10 so that dosiflextion is imposed by the platforms. The person stands and the techician positions the knees so that the medial bony surfaces are the same distance apart as the medial ankle bones. The techician then makes the necessary corrections by feeling the metatarsal joint for neutral alignment. The person can move the hips forward and backward so as to shift weight from heel to toe, which allows the fluid resin to seek equilibrium and to fill all recesses and cavities. Within or at five minutes from the first mixing and following injection of the fluid resin, the person remains still, and then for an additional short period of time in order to ensure complete curing. There is no subsequent cutting or grinding away of cured plastic material excesses.

Having described only the typical preferred forms and applications of my invention, I do not wish to be limited or restricted to the specific details herein set forth, but wish to reserve to myself any modifications or variations that may appear to those skilled in the art as set forth within the limits of the following claims.

I claim:

1. A prosthesis foot support for insertion over an interior surface of a shoe for dorsiflexed conditioning of the foot support plantar engagement with a wearer's foot, the support comprising:

a non-porous body member of flexible material for overlying the sole of the shoe, the body member having a periphery defining a front plane to underlie the metatarsal processes of the foot and a rear plane to underlie the talar heel processes of the foot, a padding member of non-porous soft material coextensive with and contiguously disposed over and separated from said non-porous body member, a liner member of supple barrier material laminated over the padding member for supportive engagement with the plantar portion of the person's foot, and having an extended marginal portion engaged over the periphery of the non-porous body member and defining an envelope between said body member and said padding member, and means for injection in situ of liquid displacement material for solidification into a dosiflexed condition with said front and rear planes angularly related.

2. The prosthesis foot support as set forth in claim 1, wherein the padding member and liner member laminated over the padding member are secured with adhesive and said marginal portion of the liner member secured to the body member.

3. The prosthesis foot support as set forth in claim 1 wherein a coupling member of loose weave cloth is laminated onto the underside of the padding member, permitting interface bonding to said injection in situ solidified material.

4. The prosthesis foot support as set forth in claim 1, wherein a coupling member of loose weave cloth is laminated onto and over the non-porous body member, permitting interface bonding to said injection in situ solidified material.

5. The prosthesis foot support as set forth in claim 1, wherein the means for injection in situ is the injection of a liquid displacement material into a side passage at an instep of the non-porous body member and opening to discharge into said envelope to occupy any space between said body member and said padding member.

6. The prosthesis foot support as set forth in claim 1, wherein the liquid displacement material is a silicon resin, there being a lateral passage centrally within the envelope as defined by said non-porous body member and said non-porous padding member for said resin injection in situ and solidification thereof.

7. A prosthesis foot support for insertion over an interior surface of a shoe for dorsiflexed conditioning of the foot support plantar engagement with a wearer's foot, the support comprising:

a non-porous body member of flexible material for overlying the sole of the shoe, the body member having a periphery defining a front plane to underlie the metatarsal processes of the foot and a rear plane to underlie the talar heel processes of the foot, a padding member of non-porous soft material coextensive with and contiguously disposed over and separated from said non-porous body member, there being at least one peripheral critical process recess in the padding member, at least one critical process cushion member of material of selected softness inserted into and occupying said at least one peripheral critical process recess, a liner member of supple barrier material laminated over the padding member and critical process cushion member for supportive engagement with the plantar portion of the person's foot, and having an extended marginal portion engaged over the periphery of the non-porous body member and defining an envelope between said body member and said padding member, and means for injection in situ of liquid displacement material for solidification into a dorsified condition with said front and rear planes angularly related.

8. The prosthesis foot support with at least one critical process cushion as set forth in claim 7, wherein the padding member has at least one metatarsal recess and a critical metatarsal process cushion member inserted into and occupying said at least one metatarsal recess.

9. The prosthesis foot support with at least one critical process cushion as set forth in claim 7, wherein the padding member has as least one talar recess and a critical talar process cushion member inserted into and occupying said at least one talar recess.

10. The prosthesis foot support with at least one critical process cushion as set forth in claim 7, wherein the padding member has at least one metatarsal recess and a critical metatarsal process cushion member inserted into and occupying said at least one metatarsal recess, and wherein the padding member has at least one talar recess and a critical talar process cushion member inserted into and occupying said at least one talar recess.

11. The prothesis foot support with at least one critical process cushion as set forth in claim 7, wherein the at least one critical process cushion member is made of permeable interconnected cell foam material for permeation with said liquid displacement material for solidification therein.

12. A prosthesis foot support for insertion over an interior surface of a shoe for stabilized dorsiflexed conditioning of the foot support plantar engagement with a wearer's foot, the support comprising:

a heel stabilizer member comprised of an upwardly open substantially rigid shell having an arch portion and an upwardly open cup portion to embrace the talar heel process of the person's foot, a non-porous body member of flexible material to overlie the sole of the shoe, and having an arch portion and a talar heel portion received in and occupying the heel stabilizer member, the porous body member having a periphery defining a front plane to underlie the metatarsal processes of the foot and a rear plane to underlie the talar heel processes of the foot, a padding member of non-porous soft material coextensive with and contiguously disposed over said non-porous body member and coextensive of the plantar portion of the person's foot including the arch and heel portions embraced within the heel stabilizer, a liner member of supple barrier material laminated over the padding member for supportive engagement with the plantar portion of the person's foot including the arch and heel portions embraced within the heel stabilizer, and having an extended marginal portion engaged over the periphery of the non-porous body member and defining an envelope between said body member and said padding member, and means for injection in situ of a liquid displacement material for solidification into a dorsiflexed condition with said front and rear planes angularly related.

13. The prosthesis foot support with a heel stabilizer member as set forth in claim 12, wherein the upwardly open shell of the heel stabilizer is defined by a bottom plantar face and a surrounding side wall extending around the posterior of the heel.

14. The prosthesis foot support with a heel stabilizer member as set forth in claim 12, wherein the heel stabilizer member is formed of a high density material and perforated for air discharge from the body member when displaced therefrom.

15. The prosthesis foot support with a heel stabilizer member as set forth in claim 12, wherein the heel stabilizer member bottom plantar face terminates in a front edge disposed beneath the metatarsal processes of the foot.

16. The prosthesis foot support with a heel stabilizer member as set forth in claim 12, wherein the bottom plantar face of the heel stabilizer member has a depending peripheral rib of increased depth as compared with a center portion thereof that is raised to form a depressible area underlying the talar processes of the foot.

17. The prosthesis foot support with a heel stabilizer member as set forth in claim 12, wherein the bottom plantar face of the heel stabilizer member has a depending peripheral rib of increased depth as compared with a center portion thereof that is raised to form a depressible area underlying the meatarsal processes of the foot.

18. The prosthesis foot support with a heel stabilizer member as set forth in claim 12, wherein the bottom plantar face of the heel stabilizer member has a depending peripheral rib of increased depth as compared with a center portion thereof that is raised to form a depressible area underlying the talar processes of the foot.

19. The prosthesis foot support with a heel stabilizer member as set forth in claim 12, wherein the bottom plantar face of the heel stabilizer member has a depending peripheral rib of increased depth as compared with a center portion thereof that is raised to form spaced and interconnecting depressible areas underlying the metatarsal and tarsal heel processes of the foot.

* * * * *